United States Patent
Sharratt et al.

(10) Patent No.: US 9,249,072 B2
(45) Date of Patent: Feb. 2, 2016

(54) PROCESS FOR THE PREPARATION OF 1,1,1-TRIFLUOROPROPANE

(75) Inventors: Andrew P. Sharratt, Cheshire (GB); Claire E. McGuinness, Cheshire (GB); Emma J. Hodgson, Cheshire (GB)

(73) Assignee: Mexichem Amanco Holding S.A. de C.V., Tlalnepantla (MX)

( * ) Notice: Subject to any disclaimer, the term of this patent is extended or adjusted under 35 U.S.C. 154(b) by 5 days.

(21) Appl. No.: 14/233,868

(22) PCT Filed: Jul. 18, 2012

(86) PCT No.: PCT/GB2012/051717
§ 371 (c)(1),
(2), (4) Date: Apr. 3, 2014

(87) PCT Pub. No.: WO2013/011311
PCT Pub. Date: Jan. 24, 2013

(65) Prior Publication Data
US 2015/0126785 A1 May 7, 2015

(30) Foreign Application Priority Data
Jul. 19, 2011 (GB) .................................. 1112370.0

(51) Int. Cl.
*C07C 17/354* (2006.01)
*C07C 19/08* (2006.01)
*C07C 17/23* (2006.01)
*C07C 17/25* (2006.01)

(52) U.S. Cl.
CPC ............... *C07C 17/354* (2013.01); *C07C 17/23* (2013.01); *C07C 17/25* (2013.01)

(58) Field of Classification Search
CPC ............................... C07C 17/354; C07C 17/25
See application file for complete search history.

(56) References Cited

U.S. PATENT DOCUMENTS

2011/0118513 A1* 5/2011 Smith et al. ................... 570/153

FOREIGN PATENT DOCUMENTS

WO    WO 2010142878 A1 * 12/2010

OTHER PUBLICATIONS

WO 2010142878 A1, Dec. 2010, pp. 1-3; English translation.*
Osborn, J. A. J. Am. Chem. Soc. 1966, pp. 1711-1732.*
Haszeldine, R.N.; "The addition of free radicals to unsaturated systems. Part I . . . " Journal of the Chem. Society, Letchworth, GB, Jan. 1, 1952, pp. 2504-2513.
E. T. McBee et al.; "Direct Bromination of Fluorinated Alkanes", Industrial & Engineering Chemistry, vol. 39, No. 3, Mar. 1, 1947, pp. 420-421.
E.T. McBee et al.; "Fluorinated Derivatives of Propane". Journal of the American Chemical Society, vol. 69, No. 4, Apr. 19, 1947, pp. 944-947.
Kraft et al "Mechanism of vinylic and allylic carbon—Fluorine bond activation of non-perfluorinated olefins using . . . " J. Am. Chem. Soc., 2002, 124(29), pp. 8681-8689.
Ng et al., "Probing the hydrophobic pocket of the active site in the particulate methane . . . " ChemBioChem, 2008, 9(7), pp. 1116-1123.
Ojima et al., "Hydroformylation of fluoro olefins . . . " J. Am. Chem. Soc., 1987, 109(25), pp. 7714-7720.
Boutevin et al., "Study of the alkylation of chlorosilanes. Part III, Synthesis and reactivity . . . ", Journal of Fluorine Chemistry, 70(1), 1995, pp. 53-57.

* cited by examiner

*Primary Examiner* — Jafar Parsa
*Assistant Examiner* — Medhanit Bahta
(74) *Attorney, Agent, or Firm* — Ryan Kromholz & Manion, S.C.

(57) ABSTRACT

The invention provides a process comprising contacting (1243zf) or (253fb) with hydrogen in the presence of a hydrogenation catalyst to produce a composition comprising 1,1,1-trifluoropropane (263fb).

13 Claims, No Drawings

PROCESS FOR THE PREPARATION OF 1,1,1-TRIFLUOROPROPANE

The invention relates to a process for the preparation of a composition comprising 1,1,1-trifluoropropane.

1,1,1-trifluoropropane is also known as HFA-263fb, HFC-263fb or simply 263fb. Hereinafter, unless otherwise stated, 1,1,1-trifluoropropane will be referred to as 263fb. The known processes for preparing 263fb typically suffer from disadvantages such as low yields, and/or the handling of toxic and/or expensive reagents, and/or the use of extreme conditions, and/or the production of toxic by-products. Methods for the preparation of 263fb have been described in, for example, Journal of Industrial and Engineering Chemistry, 1947, 39, 420-421. In this paper, 263fb is prepared by the liquid phase hydrofluorination of 1,1,1-trichloropropane, 260fb, with an antimony catalyst. However, this method is only of academic interest because of the scarcity of the 260fb feed, the hazards involved in handling the reagents and the low yields associated with the process. In addition to addressing the disadvantages of the known methods, it would be desirable to provide a new method for the preparation of 263fb that use only readily available feedstocks. The present invention seeks to address one or more of these issues.

The listing or discussion of a prior-published document in this specification should not necessarily be taken as an acknowledgement that the document is part of the state of the art or is common general knowledge.

The present invention provides a process for the production of a composition comprising 263fb by using 3,3,3-trifluoropropene (1243zf) or 3-chloro-1,1,1-trifluoropropane (253fb) as a starting material. Both of these materials are produced commercially using well known technology. 1243zf finds use as a monomer and as a working fluid in e.g. refrigeration.

The present invention provides a method for the production of a composition comprising 263fb by the hydrogenation of 1243zf.

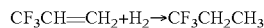

$$CF_3CH=CH_2+H_2 \rightarrow CF_3CH_2CH_3$$

In the present invention the hydrogenation of 1243zf may be carried out batch-wise or continuously, preferably continuously. Any suitable apparatus may be used, such as a static mixer, a tubular reactor, a stirred tank reactor or a stirred vapour-liquid disengagement vessel. Preferably, the apparatus is made from one or more materials that are resistant to corrosion, e.g. stainless steels, Hastelloy® or Inconel®.

The products from the hydrogenation reaction may be subjected to one or more purification steps. The purification may be achieved, for example, by separation of the desired product(s) or reagents by one or more distillation, condensation or phase separation steps and/or by scrubbing with water or aqueous base and drying with e.g. molecular sieves, zeolites or other desiccants. Any unreacted 1243zf can be recycled to the reactor where it will ultimately be converted to 263fb.

The hydrogenation reaction typically coverts at least about 50% of the starting 1243zf into 263fb, preferably at least about 75%, for example about 90%.

The hydrogenation reaction 1243zf→263fb may be carried out in the liquid or vapour phase, preferably the vapour phase. In the vapour phase a temperature of from about −40 to 150° C. may be used, e.g. from about −25 to about 100° C. Lower and higher temperatures can be used but at the expense of rate and selectivity i.e. ratio of desired product to by-products. Preferred temperatures for liquid phase hydrogenation are from about 0 to about 180° C., e.g. from about 50 to about 150° C.

If the reaction is conducted in the liquid phase any suitable solvent may be used or the reaction can be conducted in the absence of solvent, i.e. solvent free. By suitable we mean a solvent in which the reactants dissolve and in the case of homogeneous catalysts, the catalyst dissolves. The solvent should be stable to hydrogenation and should not react with either the reactants or products within the taught ranges of temperature, pressure etc. If a solvent is present it is preferred that the hydrogenation reaction is carried out in the absence of cyclohexane. This means that preferably the solvent is not cyclohexane or does not comprise cyclohexane. Suitable solvents include but are not limited to alcohols such as methanol and other suitable solvents including THF.

In another aspect of the invention the hydrogenation reaction is conducted in the presence of 263fb. 263fb can be present as a diluent in the gas phase or the liquid phase reaction. For example, in the gas phase 263fb can be used as a diluent in combination with nitrogen or instead of nitrogen. For example, in the liquid phase the reaction can take place in the presence of 263fb as a solvent alone or in combination with another solvent, such as the solvents described above. This can be achieved by any convenient means. 263fb can be introduced into the reaction vessel or zone before the start of the reaction. One or more of the starting materials can be mixed with 263fb before the start of the reaction. For example, 263fb and 1243zf can be pre-mixed and fed to the reaction vessel or zone or 1243zf can be fed to a reaction vessel or zone pre-charged with 263fb.

It has been surprisingly and unexpectedly found that conducting the hydrogenation reaction in the presence of 263fb can result in an improved yield of 263fb. The use of 263fb as can be advantageous as it avoids the need to introduce other species into the hydrogenation reaction, and can thus avoid the need for steps separate and recover the diluent. This can also reduce the likelihood of possible side reactions and therefore enhance the conversion of the feed to the desired product.

The hydrogenation reaction 1243zf→263fb may be carried out at atmospheric, sub- or super-atmospheric pressure, preferably super-atmospheric pressure. For example, the hydrogenation may be carried out at a pressure of from about 0 to about 40 bara, such as from about 1 to about 30 bara, e.g. from about 1 to about 20 bara.

The ratio of hydrogen:1243zf is suitably from about 0.1:1 to about 40:1, such as from about 1:1 to about 20:1, preferably from about 1:1 to about 10:1, e.g. from 1.5:1 to about 5:1.

Preferably the reaction is conducted in the absence of carbon dioxide.

Any suitable hydrogenation catalyst may be used. Suitable catalysts include those comprising a transition metal. Preferred transition metal hydrogenation catalysts include those comprising nickel (Ni), palladium (Pd), platinum (Pt), rhenium (Re), rhodium (Rh), ruthenium (Ru) and mixtures thereof. Such catalysts may be supported on, for example, alumina, titania, silica, zirconia or fluorides of the foregoing, calcium fluoride, carbon or barium sulphate or unsupported, for example Raney Ni and Pt produced by reducing, for example PtO$_2$. Examples of catalysts suitable for use in the present invention include Pt/alumina, Pd/barium sulphate, Pd/C, Pd and chlorotris(triphenylphosphine)rhodium(I). In one aspect the catalyst is not Pd/C. In particular, in one aspect Pd/C is not used as the catalyst in a liquid phase reaction. In a further aspect of the present invention the catalyst is platinum supported on alumina (Pt/Al$_2$O$_3$) or chlorotris(triphenylphosphine)rhodium(I) (Wilkinson's catalyst) or Adams catalyst, PtO$_2$, reduced in situ to platinum metal.

In a preferred aspect of the invention, 1243zf is hydrogenated in the liquid phase in the presence of chlorotris(triphenylphosphine)rhodium(I) (Wilkinson's catalyst), wherein the reaction is conducted in the presence of 263fb, for example, 263fb is used as a solvent or the reaction is conducted in a solvent that comprises 263fb.

When operated batchwise the hydrogenation catalyst is typically used in an amount of from about 0.01 to about 30% by weight based on the total weight of the starting materials, such as from about 0.1 to about 10%. When Pt/Al$_2$O$_3$ is used as the catalyst, the Pt is present in an amount of from about 0.01 to about 10% by weight of the catalyst, such as from about 0.1 to about 5%.

For continuous operation there should be sufficient catalyst mass to allow commercially significant conversion to be achieved across the range contact times and conditions specified.

Preferably the catalyst is stable in the presence of HF.

In the vapour phase the contact time for the hydrogen and catalyst with 1243zf is typically from about 1 to about 200 seconds, such as from about 2 to about 150 seconds.

In the liquid phase the contact time for the hydrogen and catalyst with 1243zf suitably is from about 1 to about 180 minutes, such as from about 2 to about 60 minutes.

The hydrogenation reaction is exothermic. To control the exotherm that accompanies the reaction the catalyst can be diluted in an inert carrier such as alumina, carbon etc. Additionally the 1243zf feed can be diluted with an inert gas, such as nitrogen, or preferably 263fb product.

In one aspect of the invention, 1243zf is hydrogenated in the vapour phase in the presence of a transition metal catalyst selected from those comprising nickel (Ni), palladium (Pd), platinum (Pt), rhenium (Re), rhodium (Rh), ruthenium (Ru) and mixtures thereof, preferred catalysts for this reaction include Pt on alumina catalysts. Optionally this reaction may be conducted in the presence of 263fb.

In another aspect 1243zf is hydrogenated in the liquid phase in the presence of a transition metal catalyst selected from those comprising nickel (Ni), palladium (Pd), platinum (Pt), rhenium (Re), rhodium (Rh), ruthenium (Ru) and mixtures thereof, preferred catalysts for this reaction include Adam's catalyst (Pt(IV) oxide) or Wilkinson's catalyst (RhCl(PPh$_3$)$_3$).

Suitable solvents for use in this reaction include alcohols such as methanol or THF. Optionally this reaction may be conducted in the presence of 263fb.

In another aspect 1243zf is hydrogenated in the liquid phase in the presence of a Pd catalyst such as Pd on carbon catalyst in the present of 263fb.

In another aspect for the preparation of 263fb the process comprises (i) providing a mixture of 263fb and 1243zf; and (ii) contacting the mixture with hydrogen in the presence of a suitable catalyst. Typically a transition metal catalyst selected from those comprising nickel (Ni), palladium (Pd), platinum (Pt), rhenium (Re), rhodium (Rh), ruthenium (Ru) and mixtures thereof, preferred catalysts for this reaction include Adam's catalyst (Pt(IV) oxide) or Wilkinson's catalyst (RhCl(PPh$_3$)$_3$).

The present invention also provides a method for the production of a composition comprising 263fb by the reductive dehydrochlorination of 253fb.

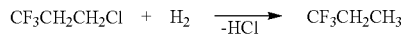

In the present invention the reductive dehydrochlorination of 253fb may be carried out batch-wise or continuously, preferably continuously. Any suitable apparatus may be used, such as a static mixer, a tubular reactor, a stirred tank reactor or a stirred vapour-liquid disengagement vessel. Preferably, the apparatus is made from one or more materials that are resistant to corrosion, e.g. stainless steels, Hastelloy® or Inconel®.

The products from the dehydrochlorination reaction may be subjected to one or more purification steps. The purification may be achieved, for example, by separation of the desired product(s) or reagents by one or more distillation, condensation or phase separation steps and/or by scrubbing with water or aqueous base.

The product of the dehydrochlorination reaction may comprise both 1243zf and 263fb and HCl. These may be separated from each other (e.g. by distillation, scrubbing with water and/or bases e.g. sodium hydroxide, calcium hydroxide etc) before the 263fb is purified by any known method such as distillation. Unreacted 253fb and any 1243zf product can be recycled to the reactor where they will be converted to 263fb.

The dehydrochlorination reaction may be carried out in the liquid or vapour phase, preferably the liquid phase. A temperature of from about −25 to about 300° C. may be used. Preferred temperatures for liquid phase dehydrochlorination are from about 0 to about 180° C., e.g. from about 15 to about 120° C. Preferred temperatures for vapour phase dehydrochlorination are from about 0 to about 300° C., such as from about 20 to about 250° C., e.g. from about 50 to about 200° C.

If the reaction is conducted in the liquid phase any suitable solvent may be used or the reaction can be conducted in the absence of solvent, i.e. solvent free. By suitable we mean a solvent in which the reactants dissolve and in the case of homogeneous catalysts, the catalyst dissolves. The solvent should be stable to hydrogenation and should not react with either the reactants or products within the taught ranges of temperature, pressure etc. Suitable solvents include but are not limited to alcohols such as methanol and other suitable solvents including THF.

In another aspect of the invention the hydrogenation reaction is conducted in the presence of 263fb. 263fb can be present as a diluent in the gas phase or the liquid phase reaction. For example, in the gas phase 263fb can be used as a diluent in combination with nitrogen or instead of nitrogen. For example, in the liquid phase the reaction can take place in the presence of 263fb as a solvent alone or in combination with another solvent, such as the solvents described above. This can be achieved by any convenient means. 263fb can be introduced into the reaction vessel or zone before the start of the reaction. One or more of the starting materials can be mixed with 263fb before the start of the reaction. For example, 263fb and 253fb can be pre-mixed and fed to the reaction vessel or zone or 253fb can be fed to a reaction vessel or zone pre-charged with 263fb.

It has been surprisingly and unexpectedly found that conducting the hydrogenation reaction in the presence of 263fb can result in an improved yield of 263fb. The use of 263fb as can be advantageous as it avoids the need to introduce other species into the hydrogenation reaction, and can thus avoid the need for steps separate and recover the diluent. This can also reduce the likelihood of possible side reactions and therefore enhance the conversion of the feed to the desired product.

The dehydrochlorination reaction may be carried out at atmospheric, sub- or super-atmospheric pressure, preferably super-atmospheric pressure. For example, the dehydrochlorination may be carried out at a pressure of from about 0 to about 40 bara, such as from about 1 to about 30 bara, e.g. from about 5 to about 20 bara.

The ratio of hydrogen:253fb is suitably from about 0.1:1 to about 40:1, such as from about 1:1 to about 20:1, preferably from about 1.1:1 to about 10:1, e.g. from 1.5:1 to about 5:1.

Any suitable dehydrochlorination catalyst may be used. Suitable catalysts include those comprising a transition metal. Preferred transition metal hydrogenation catalysts include those comprising nickel (Ni), palladium (Pd), platinum (Pt), rhenium (Re), rhodium (Rh), ruthenium (Ru) and mixtures thereof. Such catalysts may be supported on, for example, alumina, titania, silica, zirconia or fluorides of the foregoing, calcium fluoride, carbon or barium sulphate or unsupported, for example Raney Ni or Pt metal produced by reduction of $PtO_2$. Examples of catalysts suitable for use in the present invention include Pt/alumina, Pd/barium sulphate, Pd/C, Pd and chlorotris(triphenylphosphine)rhodium (I). In one aspect of the present invention the catalyst is platinum supported on alumina ($Pt/Al_2O_3$) or chlorotris(triphenylphosphine)rhodium(I) (Wilkinson's catalyst) or Adams catalyst, $PtO_2$, reduced in situ to platinum metal.

In a preferred aspect of the invention, 253fb is dehydrochlorinated in the liquid phase in the presence of chlorotris(triphenylphosphine)rhodium(I) (Wilkinson's catalyst), wherein the reaction is conducted in the presence of 263fb, for example, 263fb is used as a solvent or the reaction is conducted in a solvent that comprises 263fb.

When operated batchwise the dehydrochlorination catalyst is typically used in an amount of from about 0.01 to about 30% by weight based on the total weight of the starting materials, such as from about 0.1 to about 10%. When $Pt/Al_2O_3$ is used as the catalyst, the Pt is present in an amount of from about 0.01 to about 10% by weight of the catalyst, such as from about 0.1 to about 5%.

For continuous operation there should be sufficient catalyst mass to allow commercially significant conversion to be achieved across the range contact times and conditions specified.

Preferably the catalyst is stable in the presence of HF and HCl. In the liquid phase the process can be optionally performed in the presence of a base to react with and neutralise any acidic products formed. Suitable bases include amines for example primary alkyl amines such as ethylamine, secondary alkyl amines such as diethylamine, tertiary alkyl amines such as triethylamine, and aryl amines such as pyridine.

In the vapour phase the contact time for the hydrogen and catalyst with 253fb is typically from about 1 to about 200 seconds, such as from about 2 to about 150 seconds.

In the liquid phase the contact time for the hydrogen and catalyst with 253fb suitably is from about 1 to about 180 minutes, such as from about 2 to about 60 minutes.

Another method of effecting the dehydrochlorination is by converting 253fb to 1243zf thermally or with a base (base-mediated dehydrochlorination) to yield 1243zf and then hydrogenating the 1243zf as described above. Preferably, the base is a metal hydroxide or amide (preferably a basic metal hydroxide or amide, e.g. an alkali or alkaline earth metal hydroxide or amide).

The invention will now be illustrated by the following non-limiting examples.

EXAMPLES

Example 1

0.5 g of a 1% platinum on alumina catalyst was diluted with 1.5 g alumina beads and loaded into an Inconel tubular reactor. The catalyst mass was dried under nitrogen (90 ml/min) at 200° C. for 90 minutes and then pre-treated with hydrogen (5 ml/min) at 200° C. for 60 minutes. The catalyst was then cooled to the desired reaction temperature and a mixture of hydrogen (5 ml/min) and nitrogen (90 ml/min) at 1 barg was fed to the reactor. 1243zf (5 ml/min) was introduced into the hydrogen/nitrogen stream. The reactor was then heated and samples of the reactor off-gases taken for analysis by gas chromatography:

Experiment 1

| | Reactor temp ° C. | | | | |
|---|---|---|---|---|---|
| | 26 Mole % | 36 Mole % | 45 Mole % | 55 Mole % | 65 Mole % |
| 1243zf | 9.38 | 5.88 | 4.71 | 2.61 | 1.17 |
| 263fb | 90.62 | 94.12 | 95.29 | 97.39 | 98.83 |

Experiment 2

| | Reactor temp ° C. | | | | |
|---|---|---|---|---|---|
| | 26 Mole % | 36 Mole % | 45 Mole % | 55 Mole % | 65 Mole % |
| 1243zf | 7.84 | 5.61 | 3.67 | 2.58 | 1.38 |
| 263fb | 92.16 | 94.39 | 96.33 | 97.42 | 98.62 |

Example 2

The experiment was performed as detailed in example 1 except the temperature was 40° C. and the nitrogen diluent flow was steadily reduced:

| | $N_2$ (mls/min) | | | | | | | |
|---|---|---|---|---|---|---|---|---|
| | 90 | 70 | 50 | 40 | 30 | 20 | 10 | 5 |
| ROG 1243zf | 3.4 | 3.1 | 2.3 | 1.6 | 1.5 | 0.6 | 0.4 | 0.3 |
| ROG 263fb | 96.6 | 96.9 | 97.7 | 98.4 | 98.5 | 99.4 | 99.6 | 99.7 |

Example 3

The experiment was performed as detailed in example 2 except 263fb was used as the diluent instead of nitrogen:

| | 263fb (mls/min) | | | | | | | |
|---|---|---|---|---|---|---|---|---|
| | 90 | 70 | 50 | 40 | 30 | 20 | 10 | 5 |
| ROG 1243zf | 1.2 | 0.9 | 1.0 | 0.5 | 1.3 | 0.6 | 0.2 | 0.2 |
| ROG 263fb | 98.8 | 99.1 | 99.0 | 99.5 | 98.7 | 99.4 | 99.8 | 99.8 |

Example 4

2.0 g of a 1% platinum on alumina catalyst was loaded into an Inconel tubular reactor. The catalyst mass was dried under nitrogen (90 ml/min) at 200° C. for 90 minutes and then pre-treated with hydrogen (5 ml/min) at 200° C. for 60 minutes. The catalyst was then maintained at 200° C. and a mixture of hydrogen (5 ml/min) and nitrogen (60 ml/min) at 1 barg was fed to the reactor. 253fb (5 ml/min) was introduced into the hydrogen/nitrogen stream. Samples of the reactor off-gases taken for analysis by gas chromatography: 253fb: 84 mol %, 263fb 14.1 mol %, 1243zf 0.98 mol %.

Example 5

Liquid Phase Hydrogenation of 1243zf to 263fb using Adam's Catalyst 0.02 g of platinum(IV) oxide (Adam's catalyst) and methanol (10 mL) were loaded into a 50 mL reactor base and sealed before purging with $N_2$ gas. The reactor contents were stirred at 1000 rpm and heated to 30° C. After venting the $N_2$, 1243zf (2.158 g) was fed into the reactor followed by $H_2$ (150 mL @ 5.5 barg) and the reaction commenced. The progress of the reaction was monitored by FTIR spectroscopy. FTIR showed that the 1243zf had been hydrogenated after 35 minutes. The contents of the reactor were recovered and analysed by gas chromatography. 1243zf conversion to 263fb was greater than 99%.

Example 6

Liquid Phase Hydrogenation of 1243zf to 263fb using Wilkinson's Catalyst 0.05 g of Wilkinson's catalyst ($RhCl(PPh_3)_3$) and THF (10 mL) were loaded into a 50 mL reactor base and sealed before purging with $N_2$ gas. The reactor contents were stirred at 1000 rpm and maintained at 25° C. After venting the $N_2$, 1243zf (2.531 g) was fed into the reactor followed by $H_2$ (150 mL @ 6.5 barg) and the reaction commenced. The progress of the reaction was monitored by FTIR spectroscopy. FTIR showed complete hydrogenation of 1243zf within 4 hours 20 minutes. The contents of the reactor were recovered and analysed by gas chromatography. 1243zf conversion to 263fb was greater than 93%.

Example 7

0.4 g of a 10 wt % palladium on carbon catalyst and THF (10 mL) were loaded into a 50 mL reactor base, and sealed, before purging with $N_2$ gas. The reactor was heated to 50° C. and the contents stirred at 500 rpm. After venting the $N_2$, 1243zf (2.159 g) was fed into the reactor. $H_2$ (150 ml @ 6 barg) was then fed into the reactor and the reaction commenced. The progress of the reaction was monitored by FTIR spectroscopy. Within 7 minutes the $H_2$ has been consumed as observed by a loss of pressure, and FTIR showed some but not all of the 1243zf had been hydrogenated. Additional $H_2$ (4 barg) was fed into the reactor. Within a further 10 minutes the additional $H_2$ had been consumed. The contents of the reactor were recovered and analysed by gas chromatography: 77.6% 263fb and 22.4% 1243zf.

Example 8

0.4 g of a 10 wt % palladium on carbon catalyst was loaded into a reactor base, and sealed, before purging with $N_2$ gas. After venting the $N_2$, a mixture of 1243zf (2.24 g) and 263fb (24.62 g) was fed into the reactor. $H_2$ (150 ml @ 6.5 barg) was fed into the reactor and was heated to 50° C. and the contents stirred at 300 rpm. The progress of the reaction was monitored by FTIR spectroscopy. After 1 hour the experiment was stopped and the reaction mixture recovered for analysis: 99.63% 263fb and 0.21% 1243zf.

The invention claimed is:

1. A process for the preparation of a composition comprising 1,1,1-trifluoropropane (263fb), comprising the step of:
    reacting one of 3,3,3-trifluoropropene (1243zf) or 3-chloro-1,1,1-trifluoropropane (253fb) with hydrogen in the presence of a catalyst and in the presence of 263fb to produce 1,1,1-trifluoropropane (263fb), wherein 263fb is introduced into the reaction vessel or zone in which the reaction is conducted before the start of the reacting step.

2. A process according to claim 1, wherein said process is conducted in the vapor phase.

3. A process according to claim 1, said process further comprising the steps of:
    (i) providing a mixture of 263fb and at least a portion of said 1243zf; and
    (ii) contacting said mixture with said hydrogen.

4. A process according to claim 1, wherein said reacting step is carried out at a temperature of from about −25 to about 300° C. and a pressure of from about 0 to about 40 bara.

5. A process according to claim 2, wherein the reacting step is carried out at a temperature of from about 0 to about 300° C.

6. A process according to claim 5, wherein the reacting is carried out at a temperature of from about 20 to about 200° C.

7. A process according to claim 6, wherein the reacting is carried out at a temperature of from about 50 to about 150° C.

8. A process according to claim 1 comprising reaction of 1243zf with said hydrogen, wherein the molar ratio of hydrogen: 1243zf is from about 1:1 to about 40:1.

9. A process according to claim 1, comprising the reaction of 253fb with said hydrogen, wherein the molar ratio of hydrogen: 253fb is from about 1:1 to about 40:1.

10. A process according to claim 1 wherein said catalyst comprises one of a supported or unsupported transition metal selected from Ni, Pd, Pt, Re, Rh, Ru and mixtures thereof.

11. A process according to claim 10, wherein said catalyst is supported on at least one of alumina, titania, silica, zirconia or fluorides of the foregoing, calcium fluoride, carbon or barium sulphate.

12. A process according to claim 10, wherein said catalyst is
    (a) platinum supported on alumina Pt/Al2O3; or
    (b) chlorotris(triphenylphosphine)rhodium(I).

13. A process according to claim 1, wherein said process is carried out in the liquid phase in a solvent comprising 263fb and in which said catalyst is chlorotris(triphenylphosphine) rhodium(I) (Wilkinson's catalyst).

* * * * *